US010054530B2

(12) United States Patent
Swanner, Jr. et al.

(10) Patent No.: US 10,054,530 B2
(45) Date of Patent: Aug. 21, 2018

(54) PARTICLE DETECTION SYSTEMS

(71) Applicant: General Electric Company, Schenectady, NY (US)

(72) Inventors: Archie Lee Swanner, Jr., Easley, SC (US); Tiffany Muller Craft, Simpsonville, SC (US); Donnell Eugene Crear, Simpsonville, SC (US); Chad Joseph Dulkiewicz, Simpsonville, SC (US); Kassy Moy Hart, Greenville, SC (US)

(73) Assignee: General Electric Company, Schenectady, NY (US)

( * ) Notice: Subject to any disclaimer, the term of this patent is extended or adjusted under 35 U.S.C. 154(b) by 14 days.

(21) Appl. No.: 15/237,799

(22) Filed: Aug. 16, 2016

(65) Prior Publication Data

US 2018/0052087 A1 Feb. 22, 2018

(51) Int. Cl.
*G01N 15/02* (2006.01)
*G01N 15/14* (2006.01)

(52) U.S. Cl.
CPC ..... *G01N 15/0227* (2013.01); *G01N 15/1429* (2013.01); *G01N 2015/1493* (2013.01)

(58) Field of Classification Search
CPC ....... G01N 2015/1493; G01N 15/1429; G01N 15/0227; G01N 15/1459; G01N 2015/1486; G01N 15/1434; G01N 15/1463; G01N 15/1475; G01N 15/147; G01N 2015/1497; G01N 2015/149; G01N 15/14; G01N 21/6428; G01N 15/0211; G01N 15/1427; G01N 21/51; G01N 15/1404; G01N 21/64; G01N 2015/1402; G01N 2015/0693; G01N 2021/6421; G01N 15/12; G01N 15/1436; G01N 21/85; G01N 2015/0046; G01N 2021/4707; G01N 2015/1438; G01N 2015/144; G01N 2015/0238; G01N 15/1012; G01N 21/47; G01N 15/06; G01N 21/94; G01N 2021/6419; G01N 35/1095; G01N 21/53; G01N 2201/06113; G06K 9/2027; G06K 9/58; G06T 2207/30242; G06T 7/60; Y10T 436/101666; Y10T 428/24372; Y10T 436/25875;

(Continued)

(56) References Cited

U.S. PATENT DOCUMENTS 4,271,123 A * 6/1981 Curry .................. B01L 9/06
422/64
4,794,086 A * 12/1988 Kasper ................ G01N 15/06
356/335

(Continued)

*Primary Examiner* — Mohamed K Amara
(74) *Attorney, Agent, or Firm* — Ernest G. Cusick; Hoffman Warnick LLC

(57) ABSTRACT

Particle detection systems are disclosed. The particle detection system may include a conduit configured to receive particles removed from a component, and at least one sensor positioned adjacent the conduit. The at least one sensor may be configured to detect a particle characteristic for the particles in the conduit removed from the component. The particle detection system may also include a particle analysis system in communication with the at least one sensor. The particle analysis system may be configured to analyze the particle characteristic for the particles in the conduit to determine if the component is substantially free of particles.

16 Claims, 6 Drawing Sheets

(58) Field of Classification Search
CPC ............ G02B 21/0076; G02B 21/0004; G02B 21/365; G02B 21/16; G02B 21/06; G02B 21/361; G02B 21/0032; G03H 2001/0447; G01J 3/4406; G01J 3/02; G01J 3/36; G01J 3/10; G01J 3/2803; G01J 5/0014; G01P 5/001; G01P 3/38; G01P 3/366; G01P 3/68; G08B 17/107; G08B 17/10; G08B 21/14; G06M 1/101
See application file for complete search history.

(56) References Cited

U.S. PATENT DOCUMENTS

| | | | | |
|---|---|---|---|---|
| 4,831,867 | A * | 5/1989 | Vasseur | G01N 15/06 73/29.01 |
| 5,030,002 | A * | 7/1991 | North, Jr. | G01N 15/1404 209/3.1 |
| 5,080,866 | A * | 1/1992 | Petty | G01N 31/166 422/110 |
| 5,247,842 | A * | 9/1993 | Kaufman | B05B 5/002 356/37 |
| 5,345,079 | A * | 9/1994 | French | G01N 30/7273 250/282 |
| 5,400,665 | A * | 3/1995 | Zhu | B23K 9/328 250/288 |
| 5,481,357 | A * | 1/1996 | Ahsan | G01N 15/0205 356/246 |
| 6,081,324 | A * | 6/2000 | Yagita | G01N 21/85 356/237.1 |
| 6,334,365 | B1 * | 1/2002 | Linker | G01N 1/2214 73/864.71 |
| 7,267,798 | B2 * | 9/2007 | Chandler | G01N 15/1456 356/72 |
| 7,587,929 | B2 * | 9/2009 | Zielinski | A62B 27/00 73/46 |
| 7,724,150 | B2 * | 5/2010 | Chandler | G01N 15/0205 340/627 |
| 8,105,849 | B2 * | 1/2012 | McDevitt | B01L 3/502715 422/403 |
| 8,339,606 | B2 * | 12/2012 | Howieson | G01N 21/3504 356/432 |
| 8,363,215 | B2 * | 1/2013 | Henry | G01J 3/02 356/300 |
| 8,373,119 | B2 * | 2/2013 | Reilly | H01J 49/04 250/281 |
| 8,524,155 | B1 * | 9/2013 | Wick | G01N 1/2202 422/50 |
| 9,063,100 | B2 * | 6/2015 | Nacson | G01N 33/0004 |
| 2003/0203205 | A1 * | 10/2003 | Bi | B22F 1/0014 428/402 |
| 2004/0011974 | A1 * | 1/2004 | Matsuda | G01N 15/1436 250/574 |
| 2006/0081073 | A1 * | 4/2006 | Vandrish | G01N 1/2202 73/864.33 |
| 2010/0173394 | A1 * | 7/2010 | Colston, Jr. | B01F 3/0807 435/287.2 |
| 2010/0282960 | A1 * | 11/2010 | Clark | G01R 33/441 250/282 |
| 2011/0132108 | A1 * | 6/2011 | Novosselov | G01N 1/2202 73/863.22 |
| 2011/0222062 | A1 * | 9/2011 | Martini | G01N 21/05 356/417 |
| 2011/0294139 | A1 * | 12/2011 | Takeda | G01N 15/1484 435/7.1 |
| 2013/0270287 | A1 * | 10/2013 | Guo | G06F 17/00 221/1 |
| 2014/0076068 | A1 * | 3/2014 | Hillis | G01N 1/2202 73/863.01 |
| 2014/0076069 | A1 * | 3/2014 | Hillis | G01N 21/31 73/863.01 |
| 2014/0078493 | A1 * | 3/2014 | Hillis | G01N 21/31 356/51 |
| 2014/0366608 | A1 * | 12/2014 | Wood | G01N 33/0009 73/23.2 |
| 2015/0034606 | A1 | 2/2015 | Blackmore | |
| 2015/0177158 | A1 | 6/2015 | Cheverton | |
| 2015/0266211 | A1 | 9/2015 | Wolfgang et al. | |
| 2015/0276588 | A1 * | 10/2015 | Marshall | G01N 21/1717 250/343 |
| 2016/0109349 | A1 * | 4/2016 | Volckens | G01N 1/2202 356/318 |
| 2016/0258916 | A1 * | 9/2016 | Rodes | G01N 1/2273 |
| 2017/0184490 | A1 * | 6/2017 | Marshall | G01N 21/1717 |
| 2018/0052087 | A1 * | 2/2018 | Swanner, Jr. | G01N 15/0227 |

\* cited by examiner

PARTICLE DETECTION SYSTEMS

TECHNICAL FIELD

The disclosure relates generally to particle detection systems, and more particularly to systems for detecting particle characteristics for particles removed from components formed using additive manufacturing systems.

BACKGROUND

Components or parts for various machines and mechanical systems may be built using additive manufacturing systems. Additive manufacturing systems may build such components by continuously layering powder material in predetermined areas and performing a material transformation process, such as sintering, on the powder material. The material transformation process may alter the physical state of the powder material from a granular composition to a solid material to build the component. The components built using the additive manufacturing systems have nearly identical physical attributes as conventional components typically made by performing machining processes on stock material.

Once the additive manufactured components are built, the components undergo post-processing before being implemented or used by intended systems. One post-processing procedure that most components made from additive manufacturing typically undergo is a cleaning process. The additive manufactured components may be cleaned to remove all or substantially all debris, loose and/or excess particles or powder material from the components. Cleaning the components and removing the excess particles is crucial to ensuring the components do not cause damage within the system. Specifically, if all or substantially all excess particles are not removed from the component, the excess particles of the component may come loose and may damage the component or other portions/components of the system during assembly and/or operation.

To ensure that the additive manufactured components are adequately cleaned and/or substantially free of excess particles, additional post-processing procedures are performed after cleaning the component. In conventional procedures, the cleaned components may undergo x-ray scans using, for example, computed tomography (CT) scanning machines to ensure all or a desired amount of the excess particles are removed. The x-ray scans may determine if the additive manufactured component is substantially free of excess particles or powder material. However, where the component includes complex geometries and/or internal cavities or conduits, the x-ray scanning procedure may only be as accurate as the operational power or performance capabilities of the scanning machine. Additionally, machines capable of performing x-ray scans of the additive manufactured components are very expensive, and often require advance knowledge of the machine for proper use, calibration and maintenance. Furthermore, having to clean and subsequently scan the component adds additional steps to post-processing of the component, and ultimately results in an increase in time from when the additive manufactured component is created to when the component may be implemented within a system.

SUMMARY

A first aspect of the disclosure provides a particle detection system. The particle detection system may include a conduit configured to receive particles removed from a component, and at least one sensor positioned adjacent the conduit. The at least one sensor may be configured to detect a particle characteristic for the particles in the conduit removed from the component. The particle detection system may also include a particle analysis system in communication with the at least one sensor. The particle analysis system may be configured to analyze the particle characteristic for the particles in the conduit to determine if the component is substantially free of particles.

A second aspect of the disclosure provides a particle detection system including a vacuum conduit configured to receive particles removed from a component, an inspection conduit in fluid communication with the vacuum conduit at an inlet of the inspection conduit, and a pump in fluid communication with the vacuum conduit and the inspection conduit. The pump may be configured to move at least a portion of the particles from the vacuum conduit to the inspection conduit. The particle detection system may also include an emitter component positioned adjacent the inspection conduit. The emitter component may be configured to emit a signal through the inspection conduit. Additionally, the particle detection system may include a sensor positioned adjacent the inspection conduit, opposite the emitter component. The sensor may be configured to receive the signal emitted by the emitter component. Further, the particle detection system may include a particle analysis system in communication with the emitter component and the sensor. The particle analysis system may be configured to analyze a particle characteristic for at least the portion of the particles in the inspection conduit to determine if the component is substantially free of particles.

A third aspect of the disclosure provides a system including a support configured to receive an additive manufactured component, and an gas supply positioned adjacent the support. The gas supply may be configured to provide a gas to remove particles from the surface of the additive manufactured component. The system may also include a vacuum positioned adjacent the support, where the vacuum configured to receive the particles removed from the surface of the additive manufactured component. Additionally, the system may include a particle detection system in communication with the vacuum. The particle detection system may include a conduit in fluid communication with the vacuum, the conduit configured to receive the detached particles from the vacuum, an emitter component positioned adjacent the conduit, the emitter component configured to emit a signal through the conduit, and a sensor positioned adjacent the conduit, opposite the emitter component. The sensor may be configured to receive the signal emitted by the emitter component. Additionally, the particle detection system may also include a particle analysis system in communication with the emitter component and the sensor. The particle analysis system may be configured to analyze a particle characteristic for the particles received by the conduit to determine if the additive manufactured component is substantially free of particles.

BRIEF DESCRIPTION OF THE DRAWINGS

The disclosure will be readily understood by the following detailed description in conjunction with the accompanying drawings, wherein like reference numerals designate like structural elements, and in which.

Figure 1:
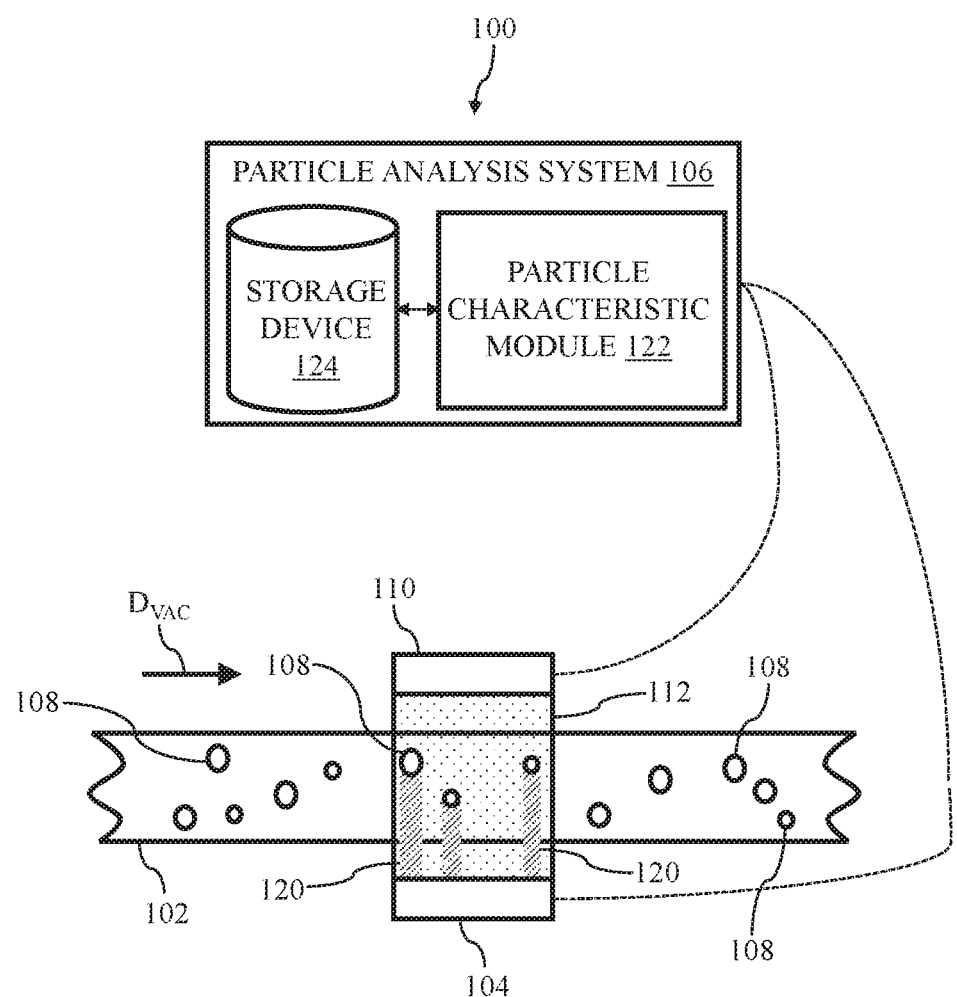
FIG. 1 depicts a side view of a particle detection system including a portion of a vacuum conduit, a sensor and a particle analysis system, according to embodiments.

It is noted that the drawings of the invention are not necessarily to scale. The drawings are intended to depict only typical aspects of the invention, and therefore should not be considered as limiting the scope of the invention. In the drawings, like numbering represents like elements between the drawings.

DETAILED DESCRIPTION

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

The following disclosure relates generally to a particle detection systems, and more particularly to systems for detecting particle characteristics for particles removed from components formed using additive manufacturing systems.

These and other embodiments are discussed below with reference to FIGS. 1-6. However, those skilled in the art will readily appreciate that the detailed description given herein with respect to these Figures is for explanatory purposes only and should not be construed as limiting.

FIG. 1 depicts a particle detection system 100, according to embodiments. Specifically, FIG. 1 depicts a side view of a portion of a vacuum conduit 102, a sensor 104 positioned adjacent conduit 102 and a particle analysis system 106 in communication with sensor 104. As discussed herein, particle detection system 100, and the various components of particle detection system 100, may be utilized to determine if a component made using additive manufacturing processes is substantially clear and/or free of material particles 108 used to build the component.

As discussed herein, additive manufacturing processes for building an additive manufactured component (see, FIG. 6; 202) may include continuously layering material particles or powder material in predetermined areas and performing a material transformation process, such as melting or sintering, on the material particles. The material transformation process may alter the physical state of the material particles from a granular composition to a solid material to build the component. Additive manufacturing of a component may utilize various distinct types of materials or compositions for building the component. As such, "particles" or "material particles" discussed herein may be any suitable material, composition and/or material particles used and/or capable of being used to build a component. In non-limiting examples, particles 108 may include, but are not limited to, metal material particles, metal-allow material particles, polymer material particles and ceramic material particles.

As shown in FIG. 1, particle detection system 100 may include a vacuum conduit 102. Vacuum conduit 102 of particle detection system 100 may be any suitable conduit, hose or supply line configured to and/or capable of receiving and/or transporting particles 108. Vacuum conduit 102 may include a predetermined size or geometry (e.g., diameter, width, length) that may allow vacuum conduit 102 to adequately receive an anticipated amount of particles 108 that may be removed from an additive manufactured component during a cleaning process, as discussed herein. The predetermined size may be based on the type, size and/or composition of particles 108 used to form the additive manufactured component, and may substantially prevent clogging and/or obstruction caused by particles 108 as particles 108 move through vacuum conduit 102.

Additionally, vacuum conduit 102 may be formed from any material that may allow for inspection and/or detection of particles 108 within vacuum conduit 102, as discussed herein. In a non-limiting example, vacuum conduit 102 may be formed from a substantially clear or transparent material (e.g., polymer). As discussed herein, the transparency of vacuum conduit 102 may allow for sensor 104 to inspect and/or detect particles 108, and specifically particle characteristics associated with particles 108, as particles 108 move through vacuum conduit 102. Although shown as one piece, vacuum conduit 102 may be formed from distinct and/or separate pieces or conduits, where each piece may include a distinct material that may aid in detection of particles 108. In another non-limiting example (not shown), vacuum conduit 102 may include a first portion formed from a substantially opaque material (e.g., polymer) and a second portion formed from a substantially transparent material (e.g., glass). In the non-limiting example, and as discussed in detail below, sensor 104 of particle detection system 100 may be positioned adjacent the second portion (e.g., glass) of vacuum conduit 102 to inspect particles 108 moving through the second portion of vacuum conduit 102.

As shown in FIG. 1, particles 108 may move or flow through vacuum conduit 102 in a direction ($D_{vac}$). Specifically, particles 108 may move or flow through conduit in direction ($D_{vac}$) toward and/or past sensor 104 in order for sensor 104 to inspect and/or detect particles 108 and particle characteristics for particle 108. Particles 108 may be moved through vacuum conduit 102 in direction ($D_{vac}$) using any suitable component or technique. In a non-limiting example, and as discussed herein, vacuum conduit 102 may be coupled to and/or in fluid communication with a vacuum system, which may move particles 108 into and/or through vacuum conduit 102 using suction and/or air propulsion. The vacuum system coupled to vacuum conduit 102 may be part of a larger component cleaning system (see, FIG. 6) for the additive manufactured component that may vacuum particles 108 removed from the component during the component cleaning process. Once particles 108 move in direction ($D_{vac}$) past sensor 104 and/or are positioned downstream of sensor 104, vacuum conduit 102 moves or carries particles 108 to be disposed of, away from sensor 104 and/or the additive manufactured component.

As discussed herein, particles 108 include any material particles of a suitable powder material or composition that may be utilized to form a component using an additive manufacturing process. As shown in FIG. 1, particles 108 in vacuum conduit 102 may be material particles that have been removed and/or cleaned from the additive manufactured component during a cleaning process. These particles 108 may be removed from the component and subsequently moved into vacuum conduit 102 to be inspected, detected and carried away from the component. Particles 108 may be substantially unique in shape and/or size (see, FIG. 1), or alternatively, may be substantially uniform in shape and/or size. The shape and/or size of particle 108 may be dependent, at least in part, on the composition of material particles 108 and/or the physical state of particles 108. In a non-limiting example, where material particles 108 are particles of aluminum, the size and/or shape of particles 108 may be substantially uniform. In another non-limiting example, where the physical state of some of particles 108 has been changed, altered or transformed (e.g., no-longer powder material), the size and/or shape of particles 108 may not be substantially uniform. Specifically, the physical state of some of particles 108 may have be transformed as a result of those specific particles being sintered and/or melted due to error and/or over-forming by the additive manufacturing system. In this non-limiting example, when the component is cleaned, these particles 108 having a transformed physical state may have a unique size and/or shape than the particles 108 which are untransformed and/or remain in a powder material state.

As shown in FIG. 1, particle detection system 100 may include at least one sensor 104. As shown in FIG. 1, sensor 104 may be positioned adjacent vacuum conduit 102. Sensor 104 may also be positioned opposite an emitter component 110 positioned adjacent vacuum conduit 102. Specifically, each of sensor 104 and emitter component 110 may be positioned adjacent vacuum conduit 102 and on opposite sides of vacuum conduit 102 such that vacuum conduit 102 is positioned between sensor 104 and emitter component 110. Additionally, and as shown in FIG. 1, sensor 104 and emitter component 110 may also be in substantial alignment with one another. Although shown and discussed herein as being positioned adjacent vacuum conduit 102, it is understood that sensor 104 and/or emitter component 110 may be positioned within partially, through and/or on vacuum conduit 102 for detecting particles 108, as discussed herein.

Sensor 104 and emitter component 110 may configured and/or utilized to inspect, detect, determine and/or measure particle characteristics of particles 108 as particles 108 flow through vacuum conduit 102. Specifically, as particles 108 move or flow through a portion of vacuum conduit 102 positioned between sensor 104 and emitter component 110, sensor 104 may detect particle characteristics of particles 108 with the aid of emitter component 110. Sensor 104 may be any suitable sensor configured to receive a signal to detect particle characteristics of particles 108. As such, emitter component 110 may be any suitable component configured to emit, generate and/or produce a signal to be received by sensor 104 to aid in the detection of particle characteristics of particles 108 by sensor 104. In a non-limiting example shown in FIG. 1, emitter component 110 may be a light source, and sensor 104 may be photoelectric or image sensor configured to receive and/or detect a light 112 emitted by the light source forming emitter component 110. Emitter component 110 configured as a light source may generate light 112 and may direct light 112 directed toward sensor 104. As discussed above, vacuum conduit 102 may be formed from a material that allows inspection and/or detection of particles 108. Specifically, and in the non-limiting example shown in FIG. 1, vacuum conduit 102 may be formed from a substantially transparent material (e.g., polymer) that may allow light 112 to pass through vacuum conduit 102 and be received and/or detected by sensor 104.

In another non-limiting example (not shown), sensor 104 may be configured as a laser sensor and emitter component 110 may be configured as a laser or an array of lasers. In an additional non-limiting example (not shown), sensor or sensor 104 may be configured as a radar sensor and emitter component 110 may be configured as a microwave component. It is understood that the configuration or component examples for sensor 104 and emitter component 110 are merely exemplary and are not limiting in anyway. Additionally, although a single sensor 104 and emitter component 110 is shown and described herein with respect to FIG. 1, it is understood that a plurality of sensors and/or a plurality of emitter components may be utilized by particle detection system 100 to detect particle characteristics for particles 108.

Figure 2:
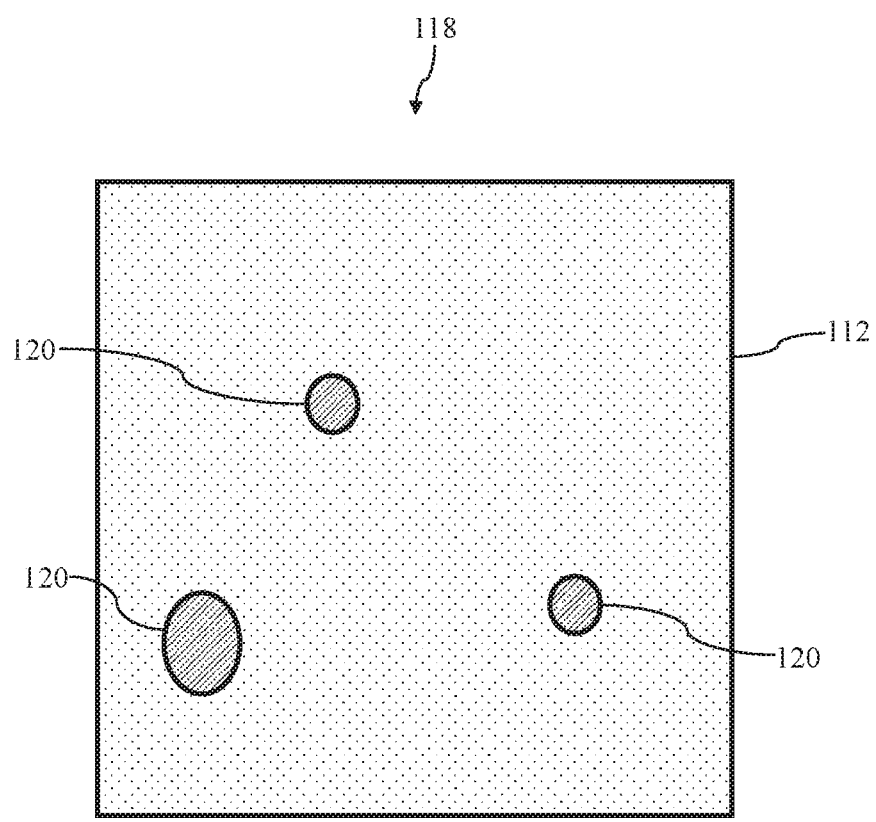
FIG. 2 depicts a top view of a light pattern or image cast on the sensor of the particle detection system of FIG. 1, according to embodiments.

Sensor 104, configured as an image sensor, may receive light 112 from emitter component 110 through vacuum conduit 102 and may detect particle characteristics of particles 108 by the portions of light that are detected and/or not detected. With continued reference to FIG. 1, FIG. 2 depicts a top view of a light pattern or a light image 118 that may be cast or projected onto sensor 104 and/or generated by sensor 104 when detecting particle characteristics of particles 108 moving through vacuum conduit 102. Light 112 generated by emitter component 110 may pass through vacuum conduit 102 and be received and/or cast on image sensor 104. Where no particle 108 is obstructing and/or blocking light 112 from reaching and/or being received by sensor 104, light may be detected by sensor 104. Conversely, where a particle 108 obstructs and/or blocks a portion of light 112, the obstructed portion of light 112 may be absorbed and/or blocked by particle 108 and/or may not be detected by sensor 104. In a non-limiting example shown in FIGS. 1 and 2, where a portion of light 112 is obstructed by particle 108, a shadow 120 may be formed, projected and/or cast on sensor 104, such that sensor 104 may not detect the portion of light 112 obstructed by particle 108. That is, shadows 120 may be formed as a result of particle 108 obstructing, absorbing, and/or blocking portions of light 112 from reach sensor 104. As discussed herein, particle detection system 100 may utilize the light pattern or light image 118 cast on and/or generated by sensor 104 to determine particle characteristics for particles 108.

Particle detection system 100 may also include particle analysis system 106. As shown in FIG. 1, particle analysis system 106 may be coupled to, operably connected to and/or in electrical communication with sensor 104 and emitter component 110. Particle analysis system 106 may be in electrical communication with sensor 104 and emitter component 110 such that sensor 104 may provide information, and/or data to particle analysis system 106 and its components for processing. In a non-limiting example, sensor 104 may provide the light pattern or light image 118 cast on and/or generated by sensor 104 to particle analysis system 106 in order for particle analysis system 106, and its various components, to determine particle characteristics for particles 108. Particle analysis system 106 may further utilize and/or analyze the particles characteristics associated with particles 108 in vacuum conduit 102 to ultimately determine if the additive manufactured component (see, FIG. 6) is substantially free of particles 108, as discussed herein.

As shown in FIG. 1, particle analysis system 106 may include a particle characteristics module 122, and a storage device 124. Particle characteristics module 122 and storage device 124 may all be operably connected and/or in electrical communication with one another. As a result, particle characteristics module 122 and storage device 124 may share, obtain and/or transfer data during the particle detection process discussed herein. Although shown as a stand-alone component and/or system, it is understood that particle analysis system 106 may be formed integrally with and/or may be a portion of an overall system or component used when cleaning the additive manufactured component. That is, particle analysis system 106 may be its own system, or alternatively, may be part of a larger system that is in communication with sensor 104 and emitter component 110, and is utilized to perform the particle detection process during a component cleaning process, as discussed herein.

Particle characteristics module 122 of particle analysis system 106 may be configured to obtain and analyze light image 118 from sensor 104 to determine particle characteristics of particles 108. Specifically, particle characteristics module 122 may determine particle characteristics for particles 108 in vacuum conduit 102 using the light 112, shadows 120, and/or light image 118 cast on and/or generated by sensor 104. The particle characteristics for particles 108 that may be determined by particle characteristic module 122 of particle analysis system 106 may include a variety of distinct characteristics relating to the physical features and/or properties of particles 108 in vacuum conduit 102. In a non-limiting example, a particle characteristic for particles 108 determined by particle characteristics module 122 may include a quantity of detected particles 108 in vacuum conduit 102. Particle characteristic module 122 may determine the quantity of detected particles 108 by analyzing light image 118 to determine how many distinct shadows 120 are formed and/or cast on sensor 104.

In another non-limiting example, a particle characteristic for particles 108 determined by particle characteristics module 122 may include a size of each detected particle 108 in vacuum conduit 102. Particle characteristic module 122 may determine the size of detected particles 108 by analyzing the dimensions and/or geometry of each shadow 120 included in light image 118. Additionally, or alternatively where the size of particles 108 is understood to be substantial uniform, particle characteristic module 122 may determine the size of detected particles 108 by obtaining size and/or dimensional information relating to particles 108 that may be stored on storage device 124, as discussed herein.

In an additional non-limiting example, a determined particle characteristic for particles 108 may include an approximate mass of detected particle 108 in vacuum conduit 102. Particle characteristic module 122 may determine the an approximate mass of detected particle 108 by analyzing and/or determining the dimensions or size of each particle 108 using shadows 120 included in light image 118 and calculating the mass based on the determined size and a predetermined weight for the material forming particles 108. The predetermined weight for the material or composition of particles 108 may be stored on storage device 124 and subsequently obtained or provided to particle characteristic module 122 after the dimensions or size of each particle 108 is determined, as discussed herein.

In a further non-limiting example, a particle characteristic for particles 108 determined by particle characteristics module 122 may include a volume or mass flow rate (e.g., mass per second) of detected particles 108 in vacuum conduit 102. Particle characteristic module 122 may determine the volume or mass flow rate of detected particles 108 by analyzing light image 118 to determine how many distinct shadows 120 are formed and/or cast on sensor 104, and how much of light 112 is received by sensor 104. That is, the volume or mass flow rate may be determined by analyzing light image 118 to determine what percentage of light 112 is blocked, obstructed and/or prevented from being received by sensor 104 as a result of particles 108 in vacuum conduit 102.

Particle characteristic module 122 may also be configured to analyze the determined particle characteristics for particles 108 in vacuum conduit 102, and determine if the additive manufactured component is substantially free of particles 108 during the cleaning process, as discussed herein. Particle characteristic module 122 may compare a desired particle characteristic threshold(s) with the determined particle characteristics of particles 108 to determine if the determined particle characteristics exceed the desired particle characteristic threshold(s). In response to the determined particle characteristics exceeding the desired particle characteristic threshold(s), particle analysis system 106 may determine that the additive manufactured component is not substantially free of particles 108, and the cleaning process of the component may continue. Conversely, in response to the determined particle characteristics not exceeding the desired particle characteristic threshold(s), particle analysis system 106 may determine that the additive manufactured component is substantially free of particles 108. As a result, the cleaning process performed on the additive manufacturing component may be stopped and/or discontinued, and the component may be ready for implementation into a system.

In a non-limiting example, the desired particle characteristic threshold may pertain to a desired size of particles 108, and specifically, the desired particle characteristic threshold may require that no detected particle 108 may be larger than 20 microns (μm). In the non-limiting example, sensor 104 may detect and/or particle characteristic module 122 may determine that detected particles 108 in vacuum conduit 102 include a size range between 40 μm and 60 μm (e.g., particle characteristic). As a result, particle characteristic module 122 may determine that the determined particle characteristic (e.g., detected particle 108 size) does exceed the desired particle characteristic threshold (e.g., desired particle size). Additionally, particle characteristic module 122 may determine that the additive manufactured component is not substantially free of particles 108, and a cleaning process of the component may continue.

In a non-limiting example, the desired particle characteristic threshold may pertain to a desired volume or mass flow rate of particles 108, and specifically, the desired particle characteristic threshold may require that the detected particles 108 may include a mass flow rate greater than 0.5 ounces (oz.) of material per second. In the non-limiting example, sensor 104 may detect and/or particle characteristic module 122 may determine that detected particles 108 in vacuum conduit 102 include a mass flow rate of approximately 0.2 oz. of material per second (e.g., particle characteristic). As a result, particle characteristic module 122 may determine that the determined particle characteristic (e.g., detected particle 108 size) does not exceed the desired particle characteristic threshold (e.g., desired particle size). Additionally, particle characteristic module 122 may determine that the additive manufactured component is substantially free of particles 108, and a cleaning process of the component may be discontinued and the component may be ready for use and/or implementation within a designated system.

Storage device 124 of particle analysis system 106 may be configured to store information and/or data relating to the particle analysis process performed by particle detection system 100 and/or particle detection system 106. Specifically, storage device 124 may be configured to store information and/or data pertaining to the material or composition of particles 108 forming the additive manufacturing component when performing the particle detection process. Additionally, storage device 124 may be configured to store information and/or data pertaining to the desired particle characteristic threshold(s) that may be based on the material or composition of particles 108. The information may be stored on storage device 124 prior to performing the particle detection process. In a non-limiting example, data relating to the predetermined and/or desired size and/or mass or particles 108 may be provided to and utilized by particle characteristic module 122 to determine particle characteristics of particles 108 detected by sensor 104, as discussed herein. Additionally, in another non-limiting example, a desired particle characteristic threshold(s) unique to the material forming particles 108 may be stored on storage device 124, and provided to and utilized by particle characteristic module 122 to determine if the particle characteristics for particles 108 exceed the desired particle characteristic threshold(s), as discussed herein.

As discussed herein, "substantially free of particles" may mean completely free of all particles 108. In this non-limiting example, particle characteristic module 122 may only determine that the additive manufactured component is substantially free of particles 108 when sensor 104 no longer detects any particles 108 and/or vacuum conduit 102 contains no particles 108. Alternatively, "substantially free of particles" may mean free of nearly all particles 108, such that any remaining particles 108 found on the additive manufactured component may impose no risk of damage to the component and/or the system utilizing the component. In this non-limiting example, particle characteristic module 122 may determine that the additive manufactured component is substantially free of particles 108 when the determined particle characteristics do not exceed the desired particle characteristic threshold(s), as discussed herein.

In a non-limiting example, sensor 104, emitter component 110 and particle analysis system 106 may continuously operate and/or function in order to continuously analyze particle characteristics for particles 108 in vacuum conduit 102. In this non-limiting example, particle analysis system 106 may be able to determine exactly when the additive manufactured component is substantially free of particles 108 (e.g., determined characteristic for particle 108 does not exceed desired particle characteristic threshold). To ensure the cleaning process is not prematurely stopped, particle analysis system 106 may continuously analyze particle characteristics for particles 108 in vacuum conduit 102 for a predetermined time after it is determined that the additive manufactured component is substantially free of particles 108. This may ensure that the additive manufactured component is substantially free of particles 108 and the risk of damage to the component and/or implementing system causes by excess particles 108 in the component is substantially reduced, minimized and/or eliminated.

In a distinct non-limiting example, sensor 104, emitter component 110 and particle analysis system 106 may operate and/or function together at predetermined intervals to analyze particle characteristics for particles 108 in vacuum conduit 102. Once particle analysis system 106 determines the additive manufactured component may be substantially free of particles 108 (e.g., determined characteristic for particle 108 does not exceed desired particle characteristic threshold), particle detection system 100, and its various components, may operate and/or perform the particle detection analysis for a predetermined number of additional intervals to ensure the cleaning process is not prematurely stopped. Performing additional particle detection analysis after it is determined that the additive manufactured component may be substantially free of particles 108 may ensure that the additive manufactured component is actually substantially free of particles 108. As a result, the risk of damage to the component and/or implementing system causes by excess particles 108 in the component may be substantially reduced, minimized and/or eliminated.

FIG. 1 depicts a non-limiting example of particle detection system 100 that may be considered an "in line" system. Specifically, FIG. 1 depicts sensor 104 and emitter 110 positioned adjacent the only conduit (e.g., vacuum conduit 102) configured to move particles 108 removed from the additive manufactured component. As such, vacuum conduit 102 and the various components (e.g., sensor 104, emitter component 110) of particle detection system 100 may be positionally linear or "in line."

Distinct from FIG. 1, FIGS. 3-5 depict "online" particle detection systems 100. That is, and with comparison to FIG. 1, sensors 104 and emitter component 110 of detection system 100 depicted in FIGS. 3-5 may be positioned adjacent an offset conduit in communication with vacuum conduit 102. It is understood that similarly numbered and/or named components may function in a substantially similar fashion. Redundant explanation of these components has been omitted for clarity.

Figure 3:
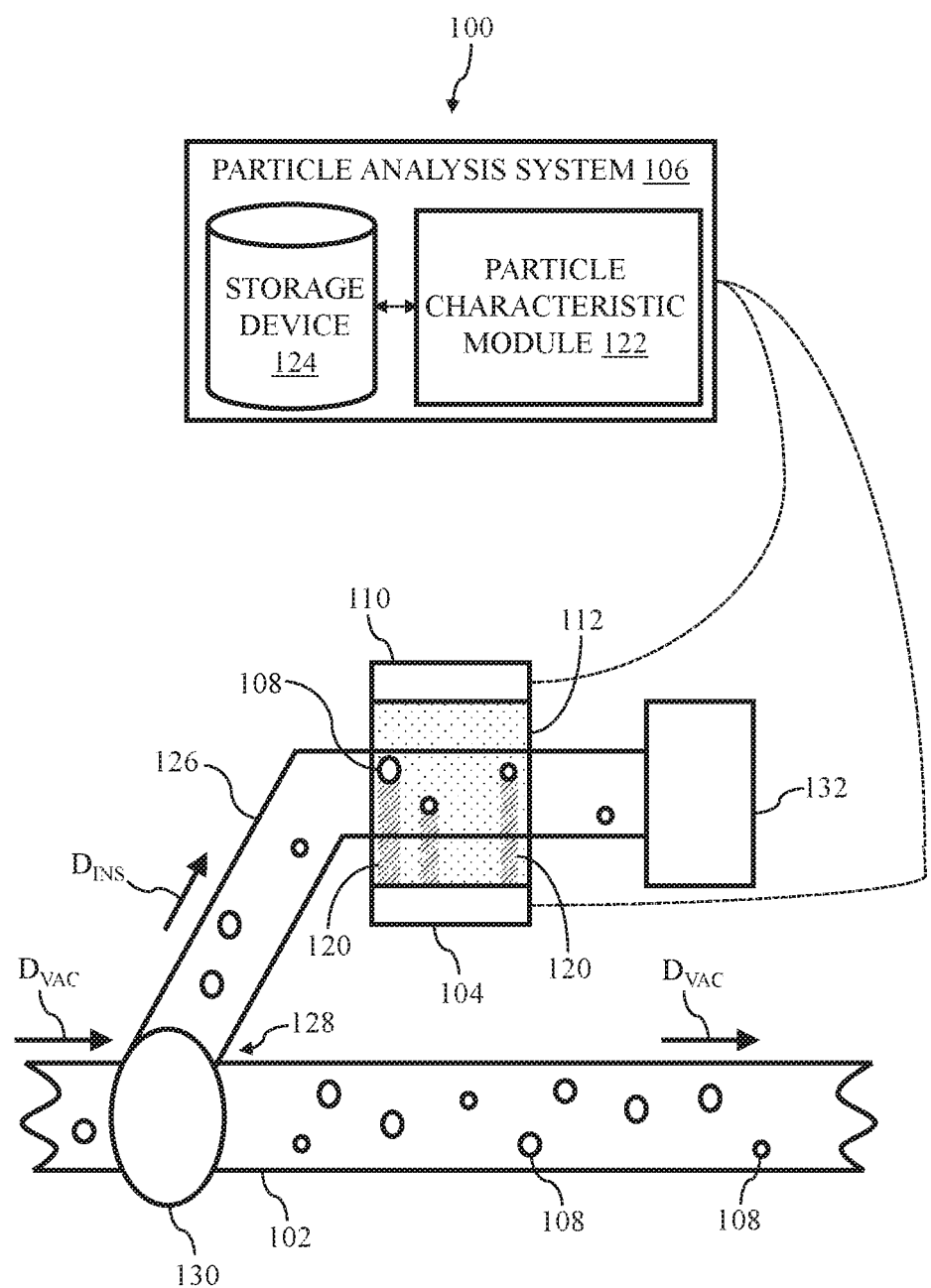
FIG. 3 depicts a side view of a particle detection system including a portion of a vacuum conduit, an inspection conduit, a sensor and a particle analysis system, according to embodiments.
Figure 4:
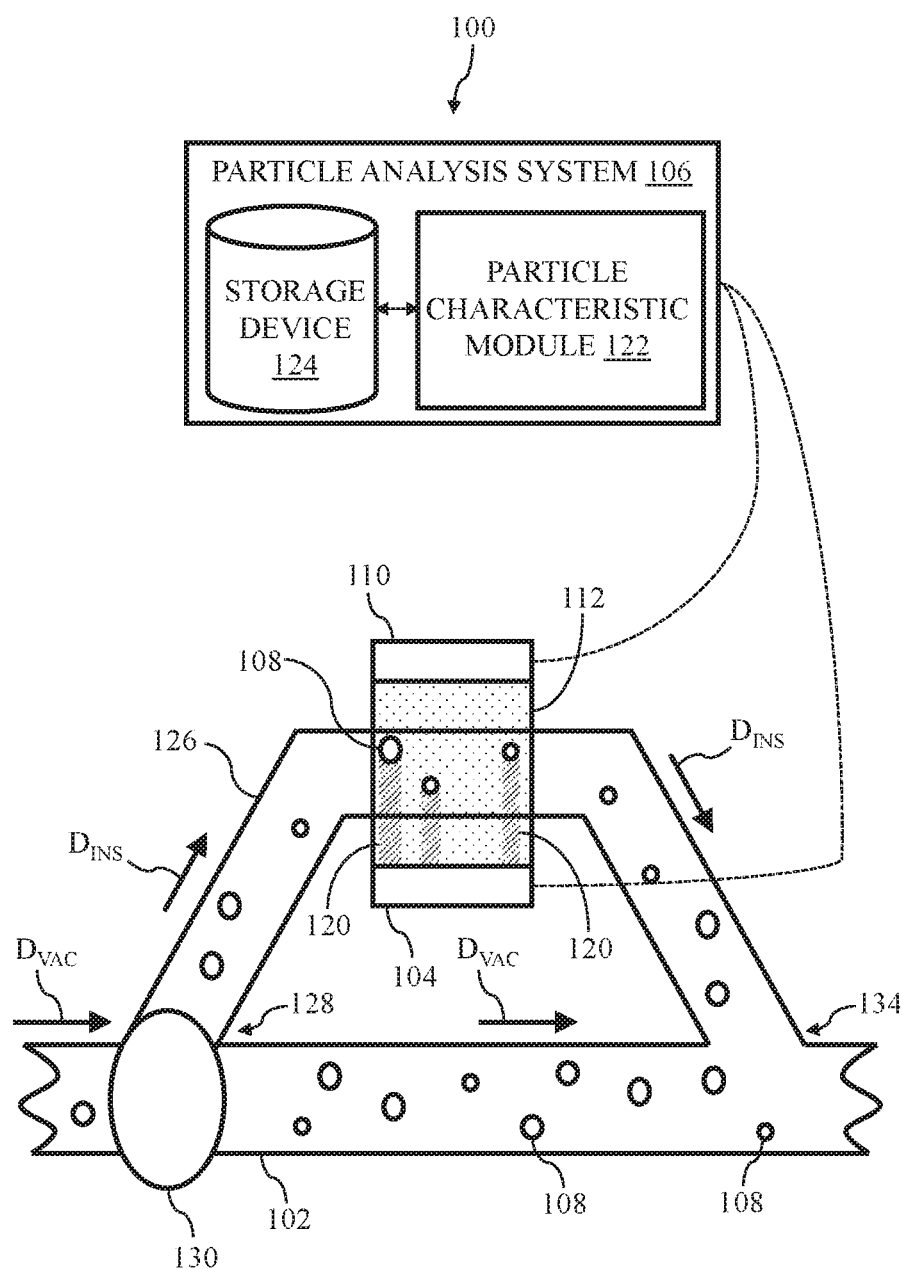
FIG. 4 depicts a side view of a particle detection system including a portion of a vacuum conduit, an inspection conduit, a sensor and a particle analysis system, according to additional embodiments.
Figure 5:
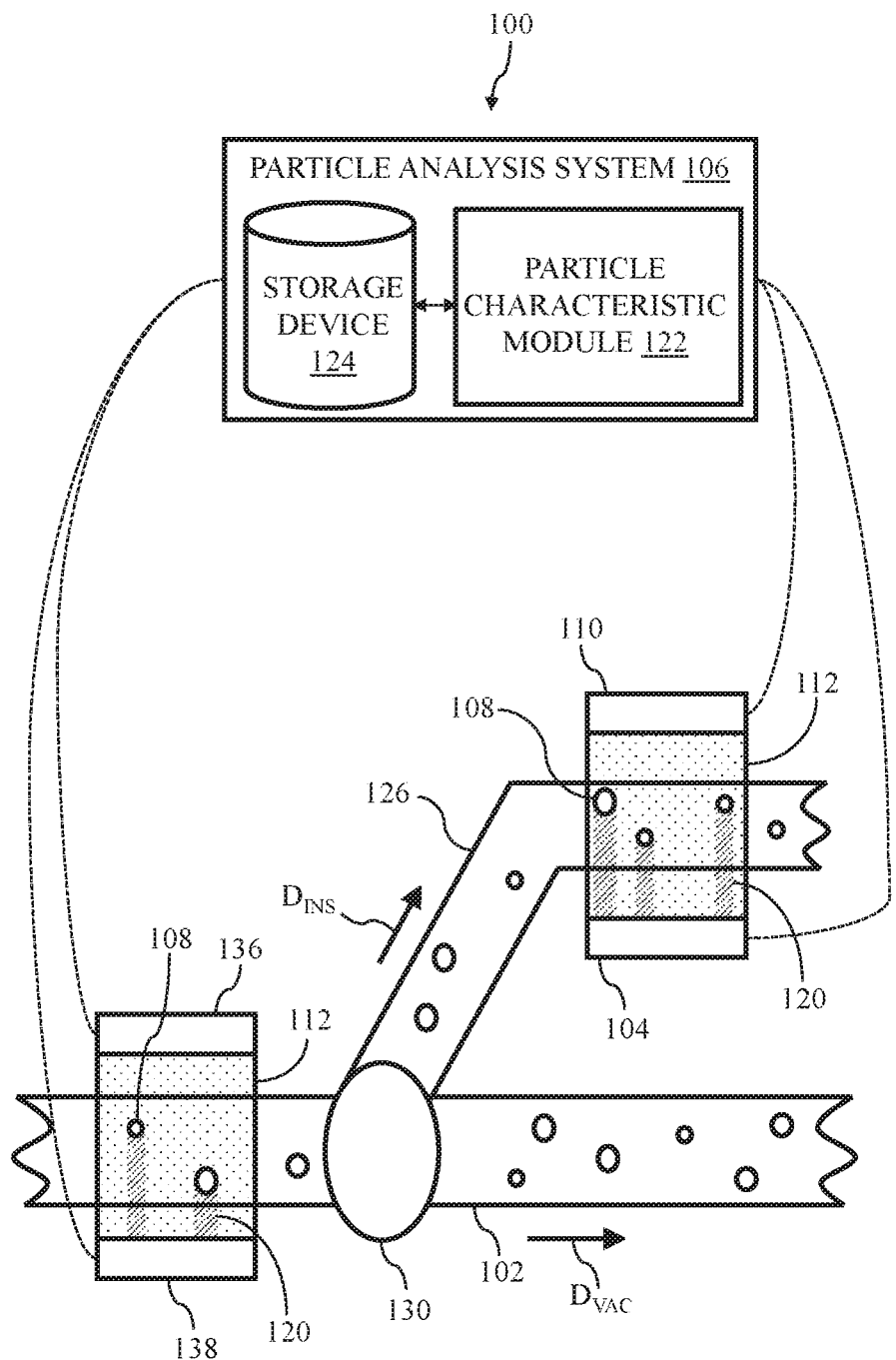
FIG. 5 depicts a side view of a particle detection system including a portion of a vacuum conduit, an inspection conduit, two distinct sensors and a particle analysis system, according to embodiments.

As shown in FIGS. 3-5, particle detection systems 100 includes an inspection conduit 126 connected to and/or in direct fluid communication with vacuum conduit 102. Inspection conduit 126 may be in fluid communication with vacuum conduit 102 via inlet 128. As shown in FIGS. 3-5, a portion of particles 108 may move from vacuum conduit 102 to inspection conduit 126. Specifically, particles 108 may move from vacuum conduit 102 into inspection conduit 126 through inlet 128, and may flow and/or pass through inspection conduit 126 in a direction ($D_{INS}$). Inspection conduit 126 may be substantially similar to vacuum conduit 102, as discussed herein with respect to FIG. 1. That is, inspection conduit 126 may include a predetermined size or geometry and may be formed from any material that may allow for inspection and/or detection of particles 108 within vacuum conduit 102, as discussed herein.

Particle detection systems 100 may also include pump 130. As shown in FIGS. 3-5, pump 130 may be in fluid communication with vacuum conduit 102 and inspection conduit 126. In a non-limiting example, pump 130 may also be configured as a junction component that may substantially couple and/or put inspection conduit 126 in fluid communication with vacuum conduit 102. Pump 130 of particle detection system 100 may be formed from any suitable material or particle pump or blower that may be configured to move at least a portion of particles 108 from vacuum conduit 102 to inspection conduit 126 to perform the particle detection process or analysis as discussed herein. In a non-limiting example, pump 130 may be configured to continuously move particles 108 from vacuum conduit 102 to inspection conduit 126 in order for particle detection system 100 to perform the particle detection process, as discussed herein. In another non-limiting example, pump 130 may be configured to move particles 108 from vacuum conduit 102 to inspection conduit 126 at predetermined intervals in order for particle detection system 100 to perform the particle detection process, as discussed herein. Regardless of pump 130 moving particles 108 from vacuum conduit 102 to inspection conduit 126 continuously or at predetermined intervals, particle detection system 100 may continuously detect particles 108, or alternatively, may detect particles 108 at predetermined intervals, as discussed herein.

Particle detection systems 100 depicted in FIGS. 3-5 may detect and/or analyze particles 108 moving and/or flowing through inspection conduit 126 in a similar manner as discussed herein with respect to FIG. 1. Specifically, particle detection systems 100, as shown in FIGS. 3-5, may include sensor 104 and emitter component 110 positioned adjacent to and/or on opposite sides of inspection conduit 126. Additionally, particle detection systems 100 shown in FIGS. 3-5 may also include particle analysis system 106, which may be coupled to, operably connected to and/or in electrical communication with sensor 104 and emitter component 110 positioned adjacent inspection conduit 126. As similarly discussed herein with respect to FIG. 1, the portion of particles 108 flowing through and/or provided to inspection conduit 126 via pump 130 may be detected, inspected and/or analyzed to determine associated particle characteristics. These detected and/or analyzed particle characteristics for particles 108 in inspection conduit 126 may be compared to desired particle characteristic threshold(s) to determine if the analyzed particle characteristics for particles 108 exceed the desired particle characteristic threshold(s). As discussed herein, the analysis and/or comparison using the particle characteristics for particles 108 in inspection conduit 126 may ultimately determine if the additive manufactured component is substantially free of particles 108.

In the non-limiting example shown in FIG. 3, particle detection system 100 may also include particle receptacle 132. Particle receptacle 132 may be in fluid communication with inspection conduit 126. Specifically, particle receptacle 132 may be in fluid communication with inspection conduit 126 and may be positioned downstream of sensor 104 and emitter component 110. Particle receptacle 132 may be formed from any suitable component that may be configured to receive particles 108 that may move and/or flow through inspection conduit 126 during the particle detection process, as discussed herein.

In another non-limiting example shown FIG. 4, inspection conduit 126 of particle detection system 100 may include outlet 134. Distinct from the non-limiting example shown in FIG. 3, inspection conduit 126 may include outlet 134, which may place inspection conduit 126 back in fluid communication with vacuum conduit 102. That is, outlet 134 of inspection conduit 126 may be in fluid communication with vacuum conduit 102. As shown in FIG. 4, outlet 134 of inspection conduit 126 may be positioned downstream of sensor 104/emitter component 110 and may carry, flow and/or move particles 108 detected in inspection conduit 126 using sensor 104 back into vacuum conduit 102. Specifically, particles 108 may move from vacuum conduit 102 into inspection conduit 126 to be inspected, and may subsequently flow and/or pass through inspection conduit 126 in a direction ($D_{INS}$) and back into vacuum conduit 102 via outlet 134 of inspection conduit 126. Once particles 108 move and/or flow back into vacuum conduit 102 via outlet 134, particles 108 may move in direction ($D_{VAC}$) through vacuum conduit 102, as discussed herein.

In the further non-limiting example shown in FIG. 5, particle detection system 100 may also include a distinct emitter component 136 and a distinct sensor 138 in addition to sensor 104 and emitter component 110. As shown in FIG. 5, distinct emitter component 136 and distinct sensor 138 may be positioned adjacent vacuum conduit 102. Specifically, distinct emitter component 136 and distinct sensor 138 may be positioned adjacent and/or on opposite sides of vacuum conduit 102, upstream of inspection conduit 126 and/or pump 130. As such, distinct emitter component 136 and distinct sensor 138 may also be positioned upstream of sensor 104 and emitter component 110 positioned adjacent inspection conduit 126.

Similar to sensor 104 and emitter component 110, distinct emitter component 136 and distinct sensor 138 may be coupled to, operably connected to and/or in electrical communication with particle analysis system 106. Additionally, distinct emitter component 136 and distinct sensor 138 may be formed from and/or configured as substantially the same components as those discussed herein with respect to sensor 104 and/or emitter component 110 (see, FIG. 1). As a result, it may be understood that distinct emitter component 136 and distinct sensor 138 may detect, inspect and/or analyze particles 108 moving through vacuum conduit 102 in a similar manner and/or fashion as discussed above. Specifically, distinct emitter component 136 and distinct sensor 138 may detect particles 108 flowing through vacuum conduit 102 to determine and/or analyze particle characteristics of particles 108. In addition, and as discussed herein, sensor 104 and emitter component 110 positioned adjacent inspection conduit 126 may also may detect particles 108 flowing through inspection conduit 126 to determine and/or analyze particle characteristics of particles 108. Each of sensor 104 and distinct sensor 138 may provide information and/or data to particle analysis system 106 to be analyzed and/or compared to determine if the additive manufactured component is substantially free of particles 108. In a non-limiting example, the information and/or data provided by both sensor 104 and distinct sensor 138 may be analyzed separately to determine if the additive manufactured component is substantially free of particles 108. In this non-limiting example, particle analysis system 106 may determine the additive manufactured component is substantially free of particles 108 when both sensor 104 and distinct sensor 138 provide information relating to the analyzed particle characteristics which do not exceed desired particle characteristic threshold(s), as discussed herein.

In another non-limiting example, one of sensor 104 or distinct sensor 138, and the information provided by the sensor relating to particles 108, may be utilized for a check and/or safety particle detection to ensure the primary sensor has properly determined the additive manufactured component is substantially free of particles 108. In this non-limiting example, sensor 104 may act as a primary sensor, and may be utilized as the primary device for determining when the additive manufactured component is substantially free of particles 108, as discussed herein. Once sensor 104 and particle analysis system 106 determine that the additive manufactured component is substantially free of particles 108, based on particles 108 in inspection conduit 126, particle analysis system 106 may engage and/or utilize distinct sensor 138 to check this determination. Specifically, particle analysis system 106 may utilize information for sensor 138 pertaining to particles 108 in vacuum conduit 102 to ensure that the determination that the additive manufactured component is substantially free of particles 108 using the information provided by sensor 106 is correct.

As similarly discussed herein, sensor 106 and distinct sensor 138 may function and/or operate continuously, or at predetermined intervals when detecting particles 108 within vacuum conduit 102 and inspection conduit 126, respectively. That is, both sensor 106 and distinct sensor 138 may operation continuously, or at predetermined intervals when particle detection system 100 is in use. Alternatively, one of sensor 104 and distinct sensor 138 may operate continuously, while the other operates at predetermined intervals, as discussed herein.

Figure 6:
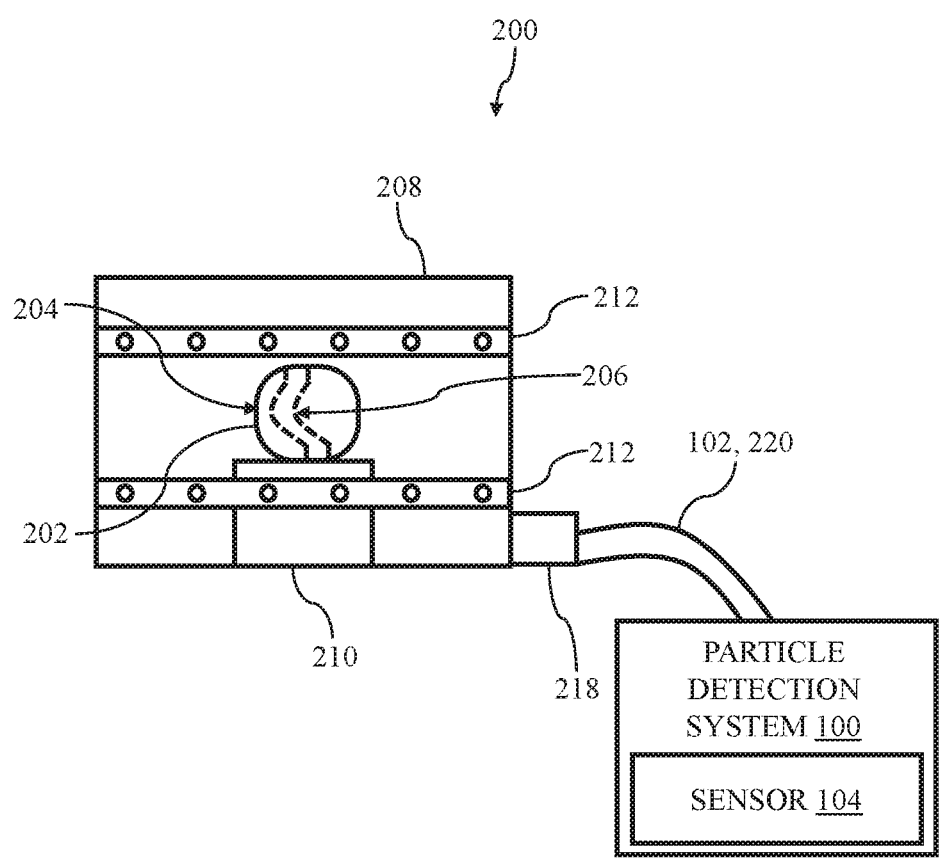
FIG. 6 depicts a front view of a cleaning system for an additive manufactured component and a particle detection system similar to the systems discussed with respect to FIGS. 1 and 3-5, according to embodiments.

FIG. 6 shows a schematic side view of an additive manufactured component cleaning system 200 (hereafter, "cleaning system 200"). As shown in FIG. 6, cleaning system 200 may include particle detection system 100, as similarly discussed herein with respect to FIGS. 1 and 3-5. Cleaning system 200 may include various components and/or may be configured to "clean" and/or substantially remove particles 108 (see, FIG. 1) from additive manufactured component 202. As discussed herein, additive manufactured component 202 may be any component made using additive manufacturing processes and/or additive manufacturing systems. As a result of being formed using additive manufacturing processes, additive manufactured component 202 may include excess particles 108 on the various surfaces 204 of component 202. Additionally, because of unique capabilities of additive manufacturing, additive manufactured component 202 may include unique and/or complex geometries or features. In a non-limiting example shown in FIG. 6, additive manufactured component 202 may include a non-linear channel 206 formed substantially through the body of additive manufactured component 202. As discussed herein, the unique and/or complex geometries or features (e.g., non-linear channel 206), and the respective surfaces 204, of additive manufactured component 202 may also include excess particles 108 that should be removed from additive manufactured component 202.

Cleaning system 200 may also include a housing 208, and a support 210 positioned within housing 208. Additive manufactured component 202 may be positioned within housing 208 of cleaning system 200 during the cleaning process. Specifically, additive manufactured component 202 may be received, held and/or supported by support 210 positioned within housing 208 during the cleaning process. Housing 208 may provide an enclosed environment for additive manufactured component 202 when performing the cleaning process to remove particles 108, as discussed herein. In a non-limiting example, housing 208 may be similar to a blasting or cleaning cabinet. Support 210 may be any component configured to receive and/or hold additive manufactured component 202 during the cleaning process performed by cleaning system 200. In a non-limiting example, support 210 may be a platform and/or pedestal that may hold and/or retain additive manufactured component 202 within housing 208. In another non-limiting example, support 210 may be a rack or track system that holds and/or suspends additive manufactured component 202 within housing 208. Support 210 may be substantially static and may rely on a user performing the cleaning process to move, adjust and/or manipulate additive manufactured component 202 within housing 208 during the cleaning process. Alternatively, support 210 may include an automated system that may move, adjust and/or manipulate the position and/or orientation of additive manufactured component 202 during the cleaning process.

Cleaning system 200 may also include a gas supply 212 positioned adjacent support 210. Specifically, gas supply 212 may be coupled to and/or positioned within housing 208 and may be positioned adjacent support 210 to provide a gas (e.g., air) to remove particles 108 from the surface 206 of additive manufactured component 202. Gas supply 212 may be any suitable component(s) configured to supply forced or compressed air to surface 206 of additive manufactured component 202 to remove particles 108. In a non-limiting example shown in FIG. 6, gas supply 212 may include a plurality of static nozzle arrays that provided compressed air to and/or within housing 208 of cleaning system 200. The nozzle arrays may provide compressed air within housing 208 that may be directed toward and/or forced onto surface 206 of additive manufactured component 202 to remove excess particles 108 during the cleaning process, as discussed herein. In another non-limiting example, gas supply may be configured as at least one sprayer that may configured to be moved and/or adjusted within housing 208 of cleaning system 200. The adjustable sprayer may move within housing 208, around support 210 and additive manufactured component 202, to remove particles 108, as discussed herein.

Additionally as shown in FIG. 6, cleaning system 200 may also include a vacuum or vacuum system 218 (hereafter, "vacuum 218"). Vacuum 218 may be positioned adjacent support 210, and may be coupled to and/or in fluid communication with housing 208 of cleaning system 200. Vacuum 218 may be in fluid communication with housing 208 to receive particles 108 removed from surface 204 of additive manufactured component 202. Specifically, once particles 108 are removed from additive manufactured component 202 using gas supply 212, vacuum 218 may receive (e.g., vacuum) particles 108 disposed of within housing 208. Vacuum 218 may ensure particles 108 may longer be capable of being reattached to surface 204 of additive manufactured component 202. Vacuum 218 may be any suitable vacuum or suction component or system configured to remove particles 108 from housing 208.

As shown in FIG. 6, vacuum 218 may be coupled to and/or in fluid communication with particle detection system 100. Specifically, vacuum 218 may be in fluid communication with particle detection system 100 to provide particle detection system 100 with particles 108 to perform the particle detection and analysis process discussed herein with respect to FIGS. 1-5. In a non-limiting example, vacuum 218 may be in direct fluid communication with particle detection system 100 via vacuum conduit 102. Specifically, vacuum conduit 102 of particle detection system 100 may be directly coupled to and/or in direct fluid communication with vacuum 218, such that particles 108 removed from housing 208 by vacuum 218 are provided and/or flow directly to vacuum conduit 102. In another non-limiting example, cleaning system 200 may include an intermediate conduit 220 that may be directly coupled to and/or in fluid communication with vacuum 218. In this non-limiting example intermediate conduit 220 may be coupled to particle detection system 100, and specifically may be in fluid communication with vacuum conduit 102, for supplying particles 108 removed from housing 208 by vacuum 218 to vacuum conduit 102 and/or particle detection system 100.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The foregoing description, for purposes of explanation, used specific nomenclature to provide a thorough understanding of the described embodiments. However, it will be apparent to one skilled in the art that the specific details are not required in order to practice the described embodiments.

Thus, the foregoing descriptions of the specific embodiments described herein are presented for purposes of illustration and description. They are not target to be exhaustive or to limit the embodiments to the precise forms disclosed. It will be apparent to one of ordinary skill in the art that many modifications and variations are possible in view of the above teachings.

We claim:

1. A particle detection system comprising:
    a vacuum conduit configured to receive particles removed from a component;
    an inspection conduit branching from and in fluid communication with the vacuum conduit at an inlet of the inspection conduit;
    a pump positioned between and coupling the vacuum conduit to the inspection conduit, the pump in fluid communication with the vacuum conduit and the inspection conduit to move at least a portion of the particles from the vacuum conduit to the inspection conduit;
    an emitter component positioned adjacent the inspection conduit, the emitter component configured to emit a signal through the inspection conduit;
    a sensor positioned adjacent the inspection conduit, opposite the emitter component, the sensor configured to receive the signal emitted by the emitter component; and
    a particle analysis system in communication with the sensor, the particle analysis system configured to:
        analyze a particle characteristic for at least the portion of the particles in the inspection conduit to determine if the component is substantially free of particles,
    wherein the pump is positioned upstream of the emitter component and the sensor.

2. The particle detection system of claim 1, wherein the pump is configured to move at least the portion of the particles from the vacuum conduit to the inspection conduit at predetermined intervals.

3. The particle detection system of claim 2, wherein the particle analysis system is further configured to analyze the particle characteristic for at least the portion of the particles at the predetermined intervals.

4. The particle detection system of claim 1, wherein the inspection conduit further comprises a disposal portion positioned downstream of the emitter component and the sensor.

5. The particle detection system of claim 1, wherein the inspection conduit further comprises an outlet positioned downstream of the emitter component and the sensor, the outlet in fluid communication with the vacuum conduit.

6. The particle detection system of claim 1, wherein the pump is configured to continuously move at least the portion of the particles from the vacuum conduit to the inspection conduit.

7. The particle detection system of claim 6, wherein the particle analysis system is further configured to continuously analyze the particle characteristic for at least the portion of the particles.

8. The particle detection system of claim 1, further comprising:
    a distinct emitter component positioned adjacent the vacuum conduit, the distinct emitter component configured to emit a signal through the vacuum conduit; and
    a distinct sensor positioned adjacent the vacuum conduit, opposite the distinct emitter component, the distinct sensor configured to receive at least a portion of the signal emitted by the distinct emitter component,
    wherein the distinct emitter component and the distinct sensor positioned adjacent the vacuum conduit are upstream of the emitter component and the sensor positioned adjacent the inspection conduit.

9. The particle detection system of claim 8, wherein the particle analysis system is in communication with the distinct sensor, and
    wherein the particle analysis system is configured to:
        analyze a distinct particle characteristic for the particles in the vacuum conduit; and
        compare the distinct particle characteristic for the particles in the vacuum conduit with the particle characteristic for at least the portion of the particles in the inspection conduit to determine if the component is substantially free of particles.

10. An additive manufactured component cleaning system comprising:
    a housing;
    a support positioned within the housing, the support configured to receive an additive manufactured component;
    a gas supply positioned within the housing, adjacent the support, the gas supply including a plurality of static nozzle arrays configured to provide a gas within the housing to remove particles from a surface of the additive manufactured component;
    a vacuum in fluid communication with the housing, the vacuum configured to receive the particles removed from the surface of the additive manufactured component; and
    a particle detection system in communication with the vacuum, the particle detection system comprising:
        a vacuum conduit in fluid communication with the vacuum, the vacuum conduit configured to receive the particles from the vacuum;
        an inspection conduit branching from and in fluid communication with the vacuum conduit at an inlet of the inspection conduit;
        a pump positioned between and coupling the vacuum conduit to the inspection conduit, the pump in fluid communication with the vacuum conduit and the inspection conduit to move at least a portion of the particles from the vacuum conduit to the inspection conduit;
        an emitter component positioned adjacent the inspection conduit, the emitter component configured to emit a signal through the inspection conduit;
        a sensor positioned adjacent the inspection conduit, opposite the emitter component, the sensor configured to receive the signal emitted by the emitter component; and
        a particle analysis system in communication with the sensor, the particle analysis system configured to:
            analyze a particle characteristic for the particles received by the inspection conduit to determine if the additive manufactured component is substantially free of particles,
        wherein the pump is positioned upstream of the emitter component and the sensor.

11. The additive manufactured component cleaning system of claim 10, wherein the particles are selected from the group consisting of: metal material particles, polymer material particles, and ceramic material particles.

12. The additive manufactured component cleaning system of claim 10, wherein the particle analysis system of the particle detection system is further configured to continuously analyze the particle characteristic of the particles in the conduit.

13. The additive manufactured component cleaning system of claim 10, wherein the particle characteristic for the particles in the conduit comprises at least one of:
- a quantity of the particles in the conduit;
- a mass of the particles in the conduit;
- a size of the particles in the conduit; and
- a volume of the particles in the conduit.

14. The additive manufactured component cleaning system of claim 10, wherein the particle analysis system of the particle detection system is further configured to:
- compare a desired particle characteristic threshold with the analyzed particle characteristic for the particles to determine if the analyzed particle characteristic exceeds the desired particle characteristic threshold.

15. The additive manufactured component cleaning system of claim 10, wherein:
- the emitter component is a light source configured to emit a light; and
- the sensor is an image sensor configured to detect the light emitted by the light source.

16. The additive manufactured component cleaning system of claim 10, wherein the particle detection system further comprises:
- a distinct emitter component positioned adjacent the vacuum conduit and upstream of the pump, the distinct emitter component configured to emit a signal through the vacuum conduit; and
- a distinct sensor positioned adjacent the vacuum conduit, opposite the distinct emitter component, the distinct sensor configured to receive at least a portion of the signal emitted by the distinct emitter component,
- wherein the particle analysis system is in communication with the distinct sensor, and is configured to:
    - analyze a distinct particle characteristic for the particles in the vacuum conduit; and
- compare the distinct particle characteristic for the particles in the vacuum conduit with the particle characteristic for at least the portion of the particles in the inspection conduit to determine if the component is substantially free of particles.

* * * * *